(12) United States Patent
Mu et al.

(10) Patent No.: US 11,958,943 B1
(45) Date of Patent: Apr. 16, 2024

(54) *ROSEIBIUM AGGREGATUM* AND USE, CULTURE METHOD AND METHOD FOR DEGRADING PLASTICS THEREOF

(71) Applicant: HAINAN TROPICAL OCEAN UNIVERSITY, Hainan (CN)

(72) Inventors: Jun Mu, Hainan (CN); Lingdi Yao, Hainan (CN); Min Liu, Hainan (CN)

(73) Assignee: HAINAN TROPICAL OCEAN UNIVERSITY, Hainan (CN)

(*) Notice: Subject to any disclaimer, the term of this patent is extended or adjusted under 35 U.S.C. 154(b) by 0 days.

(21) Appl. No.: 18/474,293

(22) Filed: Sep. 26, 2023

(30) Foreign Application Priority Data

Oct. 14, 2022 (CN) .......................... 202211258957.7

(51) Int. Cl.
 *C08J 11/10* (2006.01)
 *C12N 1/20* (2006.01)
 *C12R 1/38* (2006.01)

(52) U.S. Cl.
 CPC ............... *C08J 11/10* (2013.01); *C12N 1/20* (2013.01); *C12R 2001/38* (2021.05)

(58) Field of Classification Search
 USPC .......................................................... 521/46
 See application file for complete search history.

(56) References Cited

U.S. PATENT DOCUMENTS 6,190,903 B1    2/2001    Weinstein et al.

FOREIGN PATENT DOCUMENTS

| CN | 109749959 A | 5/2019 |
|----|-------------|--------|
| CN | 110257310 A | 9/2019 |
| CN | 113502241 A | 10/2021 |
| CN | 114958645 A | 8/2022 |
| JP | 2022139662 A | 9/2022 |

OTHER PUBLICATIONS

CNIPA First Office Action corresponding to Application No. 202211258957.7; dated Nov. 18, 2022.
Navid Taghavi et al. "Degradation of plastic waste using stimulated and naturally occurring microbial strains".
Klara Filek et al. "More than just hitchhikers: a survey of bacterial communities associated with diatoms originating from marine reptiles".
Chenxia Lu et al. "Isolation and Characterization of a Microorganism Degrading" Chin J Appl Environ Biol 2013 19 (4) : 683-687.
Hu Hao-ran, Advances in Biological Degradation of Polyvinyl Chloride, Biological Chemical Engineering vol. 6 No. 4 Aug. 2020.

*Primary Examiner* — Terressa Boykin
(74) *Attorney, Agent, or Firm* — Yue (Robert) Xu; Apex Attorneys at Law, LLP

(57) ABSTRACT

The present disclosure relates to the technical field of microbial applications, and in particular to *Roseibium aggregatum* and use, a culture method and a method for degrading plastics thereof. The *Roseibium aggregatum* provided by the present disclosure has an accession number of CGMCC No. 25240, and has a function of degrading plastic, which can degrade plastic in seawater with high degradation efficiency.

5 Claims, 4 Drawing Sheets

ROSEIBIUM AGGREGATUM AND USE, CULTURE METHOD AND METHOD FOR DEGRADING PLASTICS THEREOF

This application claims the priority of Chinese Patent Application No. 202211258957.7, filed with the China National Intellectual Property Administration on Oct. 14, 2022, and titled with "ROSEIBIUM AGGREGATUM AND USE, CULTURE METHOD AND METHOD FOR DEGRADING PLASTICS THEREOF", which is hereby incorporated by reference in its entirety.

FIELD

The present disclosure relates to the technical field of microbial application, in particular to *Roseibium aggregatum* and use, a culture method and a method for degrading plastics thereof.

BACKGROUND

Plastic has brought about earth-shaking changes to people's lives since it was invented in the early 20th century. Meanwhile, the problems caused by plastics have become more obvious and urgently need to be solved. More seriously, plastic pollution damages the marine ecosystem, and the microplastics formed by fragmentation accidentally eaten by marine organisms will further greatly endanger human health along with the food chain.

At present, there is still a lack of effective technical means to control marine plastic pollution. After the plastics enter the sea, part of it is deposited and buried in the silt near the shore or settled in the bottom mud, and the plastics floating in the sea will be corroded into microplastics over time, which makes it difficult to be salvaged and then disposed by centralized methods on land such as stacking, landfill, incineration and recycling. The method of microbial in-situ degradation and remediation has the characteristics of low cost, high benefit and environmental friendliness. However, the resources of plastic-degrading bacteria germplasm that can adapt to the marine environment are very limited at present, resulting in a large technical bottleneck in the application of in-situ remediation for marine plastic pollution.

SUMMARY

In view of this, the technical problem to be solved by the present disclosure is to provide *Roseibium aggregatum* and use, a culture method and a method for degrading plastics thereof. The *Roseibium aggregatum* MY02 provided by the present disclosure has a function of degrading plastics, which can degrade plastics in seawater with high degradation efficiency.

The present disclosure provides a method for degrading plastics, comprising contacting *Roseibium aggregatum* with plastics and degrading plastics.

The present disclosure provides *Roseibium aggregatum*, which was deposited on Jul. 6, 2022 in the China General Microbiological Culture Collection Center, Institute of Microbiology, Chinese Academy of Sciences, No. 1, Beichen West Road, Chaoyang District, Beijing, with an accession number of CGMCC No. 25240.

The *Roseibium aggregatum* and at least one of its cell components, metabolites, derivatives of metabolites, and secretions are within the protection scope of the present disclosure. It can be understood that the cell component is selected from the group consisting of a cell, a culture medium containing the cell, various chemical components that make up the cell and a combination thereof; the metabolite is selected from the group consisting of an intermediate metabolite, a final metabolite in the metabolism and a combination thereof; and the secretion is selected from the group consisting of nucleic acid, enzyme, antibody, exosome, hormone and a combination thereof.

In a specific embodiment, the *Roseibium aggregatum* in the method for degrading plastics is *Roseibium aggregatum* MY02.

In a specific embodiment, the degrading in the method for degrading plastics further comprises subjecting the *Roseibium aggregatum* to natural environment or culturing the *Roseibium aggregatum* under culture conditions.

In a specific embodiment, the culturing the *Roseibium aggregatum* in the method for degrading plastics is performed in a culture medium containing plastics.

The present disclosure provides use of the *Roseibium aggregatum* in degrading plastics. The *Roseibium aggregatum* MY02 provided by the present disclosure can utilize plastics as a carbon source and energy source, and has a function of degrading plastics with high degradation efficiency. In some embodiments of the present disclosure, the plastic is selected from the group consisting of polyethylene plastic, polypropylene plastic, polystyrene plastic and a mixture thereof, preferably polyethylene plastic. In an embodiment, the plastic is plastic particles or a plastic film. In an embodiment, the plastic is microplastic.

The present disclosure provides a method for degrading plastics, comprising degrading plastics with *Roseibium aggregatum*. In particular, the method for degrading plastics in the present disclosure comprises contacting *Roseibium aggregatum* with plastics for proliferation and degradation. The method for degrading plastics in the present disclosure can be carried out in natural environment or a culture medium. In an embodiment, the method comprises contacting *Roseibium aggregatum* with plastics and culturing *Roseibium aggregatum* in seawater for proliferation and degradation. In an embodiment, the method comprises contacting *Roseibium aggregatum* with plastics and culturing *Roseibium aggregatum* in a culture medium for proliferation and degradation. The plastics are the same as above, and will not be repeated here.

The present disclosure provides a method for culturing *Roseibium aggregatum*, comprising inoculating *Roseibium aggregatum* in a culture medium containing plastics for culture. In particular, in the present disclosure, a culture solution of *Roseibium aggregatum* is inoculated in a culture medium containing plastics for culture. In some embodiments of the present disclosure, a culture solution of *Roseibium aggregatum* is inoculated into an inorganic salt liquid culture medium containing plastics or an inorganic salt solid culture medium containing plastics for culture. In some embodiments of the present disclosure, a culture solution of *Roseibium aggregatum* is inoculated on a flat plate of an inorganic salt solid culture medium containing plastics or in a slanted test tube of an inorganic salt solid culture medium containing plastics for culture. The plastics are the same as above, and will not be repeated here. In the culture medium of the present disclosure, the mass of the plastic contained in each liter of the culture medium is 1 g-3 g, preferably 2 g.

In some embodiments of the present disclosure, *Roseibium aggregatum* is inoculated at an amount of 5%-20%, preferably 5%-10%, more preferably 10%. In some embodiments of the present disclosure, the culture is carried out at a pH value of 6-8, preferably 7. In some embodiments of the present disclosure, the culture is carried out at 10° C.-40° C. and 100 rpm-150 rpm, preferably at 28° C. and 120 rpm. In some embodiments of the present disclosure, the culture is carried out for more than 4 weeks.

In the present disclosure, the pH value in the culture process is adjusted by adjusting the pH value of the culture medium. In an embodiment, the pH of the culture medium is adjusted with 1 mol/L-3 mol/L NaOH to 6-8, preferably 7.

In some embodiments of the present disclosure, in parts by mass, the inorganic salt liquid culture medium comprises 0.5-1 part of $K_2HPO_4$, 0.5-1 part of $KH_2PO_4$, 0.8-1.2 parts of $NH_4NO_3$, 0.08-0.12 parts of $CaCl_2$, 0.01-0.04 parts of $FeSO_4$ and 500-1500 parts of seawater; and the inorganic salt solid culture medium comprises 0.5-1 part of $K_2HPO_4$, 0.5-1 part of $KH_2PO_4$, 0.8-1.2 parts of $NH_4NO_3$, 0.08-0.12 parts of $CaCl_2$, 0.01-0.04 parts of $FeSO_4$, 10-20 parts of agar and 500-1500 parts of seawater. In an embodiment, the inorganic salt liquid culture medium comprises 0.7 g of $K_2HPO_4$, 0.7 g of $KH_2PO_4$, 1.0 g of $NH_4NO_3$, 0.1 g of $CaCl_2$, 0.02 g of $FeSO_4$ and 1 L of seawater. In an embodiment, the inorganic salt solid culture medium comprises 0.7 g of $K_2HPO_4$, 0.7 g of $KH_2PO_4$, 1.0 g of $NH_4NO_3$, 0.1 g of $CaCl_2$, 0.02 g of $FeSO_4$, 15 g of agar and 1 L of sea water.

In some embodiments of the present disclosure, the *Roseibium aggregatum* is obtained by acclimating, enriching, primary-screening, and re-screening *Roseibium aggregatum* of the present disclosure in environmental samples.

Firstly, microorganisms in the environmental samples are acclimated to proliferate bacterial colonies degrading plastics. In particular, plastics are first placed in an environment for continuous in-situ acclimation. In some embodiments of the present disclosure, plastics are placed in root mud of mangrove in Sanya, Hainan to continuously acclimate the indigenous microorganisms in situ for more than 4 weeks, and then the plastic and the root mud around the plastic are taken as environmental samples.

After acclamation in the environment, bacteria with plastic-degrading activity are enriched. In particular, the environmental samples obtained after acclimation are placed in an enrichment culture medium for enrichment culture of bacteria with plastic-degrading activity. More particularly, the environmental samples obtained after acclimation are placed in an enrichment culture medium containing plastic for primary enrichment culture of bacteria with plastic-degrading activity followed by continuous passage and enrichment culture. In some embodiments of the present disclosure, the environmental samples obtained after acclimation are placed in an enrichment culture medium containing plastic, and bacteria with plastic-degrading activity are subjected to primary enrichment culture for more than 4 weeks, preferably 6 weeks, followed by continuous passage and enrichment culture for 3-5 times, preferably 3 times, wherein each continuous passage and enrichment culture is carried out for 4-6 weeks. The plastics of the present disclosure are the same as those described above, and will not be repeated here. In the culture medium of the present disclosure, the mass of the plastic contained in each liter of the culture medium is 1 g-3 g, preferably 2 g. In an embodiment, the enrichment culture is carried out at a pH value of 6-8, preferably 7. In an embodiment, the enrichment culture is carried out at 10° C.-40° C. and 100 rpm-150 rpm, preferably at 28° C. and 120 rpm. In an embodiment, the environmental samples are inoculated in the enrichment culture medium at an amount of 5-10%.

In the present disclosure, the pH value in the enrichment process is adjusted by adjusting the pH value of the enrichment culture medium. In an embodiment, the pH of the enrichment culture medium is adjusted with 1 mol/L-3 mol/L NaOH to 6-8, preferably 7.

In some embodiments of the present disclosure, in parts by mass, the enrichment culture medium comprises 0.5-1 part of $K_2HPO_4$, 0.5-1 part of $KH_2PO_4$, 0.8-1.2 parts of $NH_4NO_3$, 0.08-0.12 parts of $CaCl_2$, 0.01-0.04 parts of $FeSO_4$, 0.08-0.12 parts of yeast extract powder and 500-1500 parts of seawater. In an embodiment, the enrichment culture medium comprises 0.7 g of $K_2HPO_4$, 0.7 g of $KH_2PO_4$, 1.0 g of $NH_4NO_3$, 0.1 g of $CaCl_2$, 0.02 g of $FeSO_4$, 0.1 g of yeast extract powder and 1 L seawater.

After enrichment, bacteria with plastic-degrading activity are subjected to primary screening and re-screening to obtain *Roseibium aggregatum*. In particular, after diluting and spreading the bacteria with plastic-degrading activity obtained after the enrichment culture, the primary screening is performed by a plate streaking method, and then the re-screening culture is performed in an inorganic salt liquid culture medium to obtain a stock solution of the bacteria with plastic-degrading activity. In some embodiments of the present disclosure, the bacteria with plastic-degrading activity obtained after the enrichment culture are diluted, spread and cultured on an inorganic salt solid culture medium containing plastic for 1-2 weeks, then separated and purified using a plate streaking method according to morphology, size and color of the colony to obtain a primary-screened *Roseibium aggregatum*. Then a ring of the primary-screened *Roseibium aggregatum* is picked and subjected to re-screening culture for 1-2 weeks in an inorganic salt liquid culture medium containing plastics to obtain *Roseibium aggregatum*. In the culture medium of the present disclosure, the mass of the plastic contained in each liter of the culture medium is 1 g-3 g, preferably 2 g. In some embodiments of the present disclosure, the dilution spreading is performed at a dilution gradient of $10^{-1}$, $10^{-2}$, and $10^{-3}$. In the present disclosure, the conditions for the culture, the inorganic salt liquid culture medium, the inorganic salt solid culture medium and the plastic are independently the same as above, and will not be repeated here.

The present disclosure provides *Roseibium aggregatum* and use, a culture method, and a method for degrading plastics thereof. The *Roseibium aggregatum* MY02 provided by the present disclosure, with an accession number of CGMCC No. 25240, has a function of degrading plastics, which can degrade polyethylene in seawater with high degradation efficiency. Experiments show that the present disclosure successfully separated and screened out *Roseibium aggregatum* MY02 from bottom mud of the mangrove near the estuary of Sanya River in Hainan, and the surface of the polyethylene plastic film treated with the *Roseibium aggregatum* MY02 for 4 weeks became rough and exhibited obvious erosion holes, indicating the degradation and at a rate of $1.3 \pm 0.12$ g/(d·m$^3$), whereas the surface of the polyethylene plastic film in the control group showed no signs of erosion and no change in mass. The analysis by infrared spectroscopy further confirmed that the *Roseibium aggregatum* MY02 of the present disclosure utilizes plastics as an energy source and has a function of degrading plastics.

Biological Deposit Information

Biological material MY02, taxonomic name: *Roseibium aggregatum*, deposited on Jul. 6, 2022 in the China General Microbiological Culture Collection Center, Institute of Microbiology, Chinese Academy of Sciences, No. 1, Beichen West Road, Chaoyang District, Beijing, with an accession number of CGMCC No. 25240.

DETAILED DESCRIPTION

Figure 1:
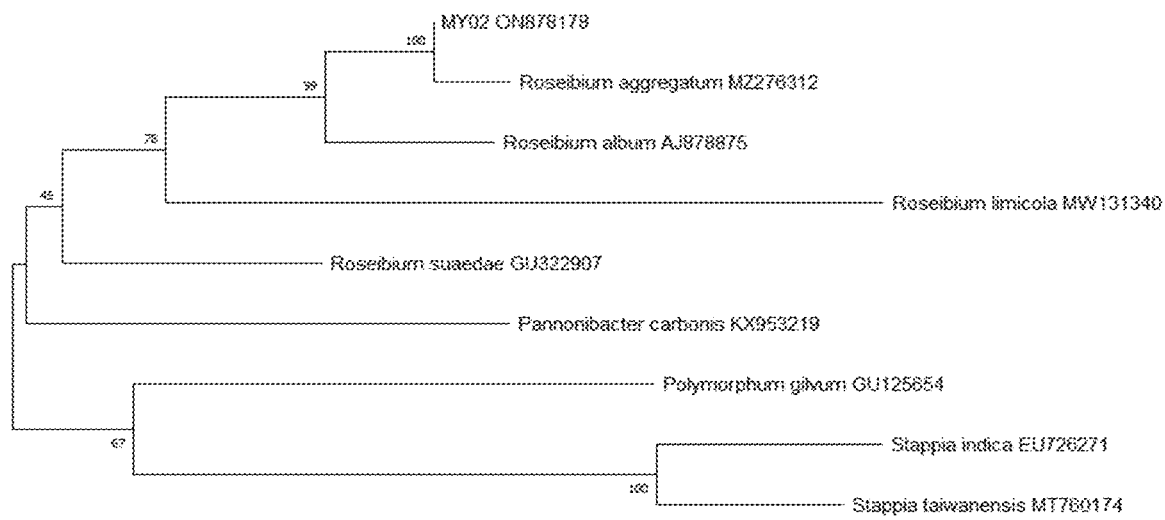
FIG. 1 is a phylogenetic tree of the bacterial strain obtained in Example 1 constructed based on the 16S rRNA gene sequence.

The present disclosure discloses *Roseibium aggregatum* and use, a culture method and a method for degrading plastics thereof. Those skilled in the art can learn from the content herein to appropriately improve the process parameters to realize the present disclosure. In particular, it should be noted that all similar replacements and modifications are apparent to those skilled in the art, and they are all considered to be included in the present disclosure. The method and use of the present disclosure have been described through preferred embodiments, and those skilled apparently can make modifications or appropriate changes and combinations of the method and use herein without departing from the content, spirit and scope of the present disclosure to realize and apply the technology of the present disclosure.

The present disclosure is further described below in conjunction with examples:

Example 1

The separation of bacteria for degrading polyethylene plastic in marine environment, including steps of in-situ acclimation and enrichment culture, was specifically as follows:

1. In-situ acclimation: In the root mud of the mangrove near the estuary of Sanya River in Sanya City, Hainan Province, polyethylene plastic film strips were buried shallowly for continuous in-situ acclimation of indigenous microorganisms and proliferation of bacterial colonies degrading plastics. The acclimation was performed for 4 weeks. Then the polyethylene plastic film and the root mud covered by it were collected as samples for the next enrichment culture.

2. Enrichment culture: Under sterile operating conditions, the samples obtained after the in-situ acclimation were taken, i.e., the polyethylene plastic film and the root mud covered by it were taken as an inoculum, where the polyethylene plastic film was cut with sterile scissors into squares of 1 cm in length and width, and then inoculated at an amount of 10% into 100 mL of sterilized primary enrichment culture medium in a 300 mL Erlenmeyer flask for 6 weeks of culture under shaking at 28° C. and 120 rpm. The sterilized primary enrichment culture medium was sterilized under high pressure at 121° C. for 20 min in advance, and added with pre-sterilized polyethylene plastic film of 1 cm in length and width at an amount of 2 g/L after cooling to room temperature. The sterilization was conducted as follows: the polyethylene plastic film was soaked in 2% SDS for 2 h followed by 75% alcohol for 2 h, and rinsed with sterile water for 3 times. For the subsequent enrichment culture, the primary enrichment culture medium with yeast extract powder removed was used for directional enrichment, and the continuous passage and enrichment were conducted for 3 times, 4 weeks for each time. The primary enrichment liquid culture medium had a formula (/L) of: 0.7 g of $K_2HPO_4$, 0.7 g of $KH_2PO_4$, 1.0 g of $NH_4NO_3$, 0.1 g of $CaCl_2$, 0.02 g of $FeSO_4$, 0.1 g of yeast extract powder and 1000 mL of naturally aged seawater, with a pH adjusted to 7.0.

After the enrichment culture, the bacteria degrading polyethylene plastic in marine environment was subjected to activity screening including steps of primary screening and re-screening, which was specifically as follows:

1. Primary screening: After the enrichment culture, the bacteria grown to the logarithmic phase in the culture solution were separated by a spread plate method at a dilution gradient of $10^{-1}$, $10^{-2}$ and $10^{-3}$. After one week of growth on a Petri dish plate, colonies with different morphologies, sizes and colors were selected and streaked on a fresh inorganic salt solid culture medium plate for 2-3 times to obtain pure bacterial strains. The inorganic salt solid culture medium had a formula (/L) of 0.7 g of $K_2HPO_4$, 0.7 g of $KH_2PO_4$, 1.0 g of $NH_4NO_3$, 0.1 g of $CaCl_2$, 0.02 g of $FeSO_4$, 15 g of agar, 1000 mL of natural seawater, and 2.0 g of PE powder (polyethylene microplastics), with a pH adjusted to 7.0 with 1 mol/L NaOH, and it was sterilized under high pressure at 121° C. for 20 min.

2. Re-screening (re-testing): In order to prevent false positive results caused by mixed colonies and agar in the inorganic salt solid culture medium, the pure strains obtained by the primary screening were re-screened (re-tested). A ring of well-grown pure strain lawn was picked and inoculated into 100 mL of inorganic salt liquid culture medium (i.e., the inorganic salt solid culture medium used for the primary screening free of agar) for 1 week of culture at 28° C. and 120 rpm to obtain a culture solution of *Roseibium aggregatum*. The culture solution of *Roseibium aggregatum* was inoculated as an inoculum onto a flat plate containing a solid culture medium, and the strains grew out after the culture were considered as effective strains. The inorganic salt liquid culture medium had a formula (/L) of 0.7 g of $K_2HPO_4$, 0.7 g of $KH_2PO_4$, 1.0 g of $NH_4NO_3$, 0.1 g of $CaCl_2$, 0.02 g of $FeSO_4$, 1 L of natural seawater, and 2.0 g of PE powder (polyethylene microplastics), with a pH adjusted to 7.0 with NaOH of 1 mol/L, and it was sterilized under high pressure at 121° C. for 20 min.

Example 2

The strain obtained in Example 1 was classified and identified as follows:

The strain obtained in Example 1 was inoculated on ocean 2216E solid culture medium for 2-3 days of growth, and then colonies on the plate were collected for extraction of bacterial nucleic acid for sequencing. The 2216E solid culture medium had a formula (/L) of 5.0 g of peptone, 1.0 g of yeast powder, 0.1 g of ferric citrate, 19.45 g of sodium chloride, 5.98 g of magnesium chloride, 3.24 g of sodium sulfate, 1.8 g of calcium chloride, 0.55 g of potassium chloride, 0.16 g of sodium carbonate, 0.08 g of potassium bromide, 0.034 g of strontium chloride, 0.022 g of boric acid, 0.004 g of sodium silicate, 0.0024 g of sodium fluoride, 0.0016 g of ammonium nitrate, 0.008 g of disodium hydrogen phosphate, 15 g of agar and 1 L of deionized water, with a pH of 7.6±0.2. Sequencing of 16S rRNA gene and homology analysis were performed as follows:

of sodium fluoride, 0.0016 g of ammonium nitrate, 0.008 g of disodium hydrogen phosphate and 1000 mL of deionized water, with a pH of 7.6±0.2.

TABLE 1

| | Time (h) | | | | | | | | | | | | | |
|---|---|---|---|---|---|---|---|---|---|---|---|---|---|---|
| | 0 | 2 | 4 | 6 | 8 | 10 | 12 | 14 | 18 | 22 | 26 | 30 | 34 | 38 |
| $OD_{600}$ | 0.187 | 0.275 | 0.532 | 0.842 | 0.992 | 1.173 | 1.230 | 1.272 | 1.344 | 1.427 | 1.499 | 1.500 | 1.500 | 1.501 |

DNA of the single bacterial strain screened from Example 1 was extracted using TSINGKE Plant DNA Extraction Kit (General Type) to obtain a DNA sample of the bacterial strain. The extracted DNA sample was appropriately diluted to serve as a PCR template, and PCR amplification was performed to amplify 1500 bp in length using the bacterial universal primers 27F (5'-AGTTTGATCMTGGCTCAG-3') and 1492R (5'-GGTTACCTTGTTCGACTT-3'). The amplification system included: 45 μL of 1×TSE101 gold mix, 2 μL of primer 27F, 2 μL of primer 1492R, and 1 μL of DNA template. The amplification program included: pre-denaturation at 98° C. for 2 min; 35 cycles of 98° C. for 10 s, 56° C. for 10 s, and 72° C. for 10 s; extension at 72° C. for 5 min, and storage at 4° C. The amplified PCR product was subjected to agarose gel electrophoresis (2 μL sample+6 μL bromophenol blue) at 300 V for 12 min to obtain an identification gel map. The prepared PCR product was sent to Sequencing Department of Guangzhou Tsingke for the first generation sequencing. The resulting sequences were assembled by ContigExpress, and the unaligned parts at both ends were removed. The assembled sequence was aligned in EzBioCloud, and found to have a 100% similarity with *Roseibium aggregatum*. A phylogenetic tree of the bacterial strain was constructed based on the 16S rRNA gene sequence, as shown in FIG. 1. FIG. 1 is a phylogenetic tree of the bacterial strain obtained in Example 1 constructed based on the 16S rRNA gene sequence, which shows that the bacterial strain obtained in Example 1 was clustered in the same branch with *Roseibium aggregatum* on the phylogenetic tree. The bacterial strain obtained in Example 1 was uploaded to NCBI and a registration number of ON878178 was obtained.

Figure 2:
FIG. 2 shows the morphology of the bacterial strain obtained in Example 1 in 2216E solid culture medium.
Figure 3:
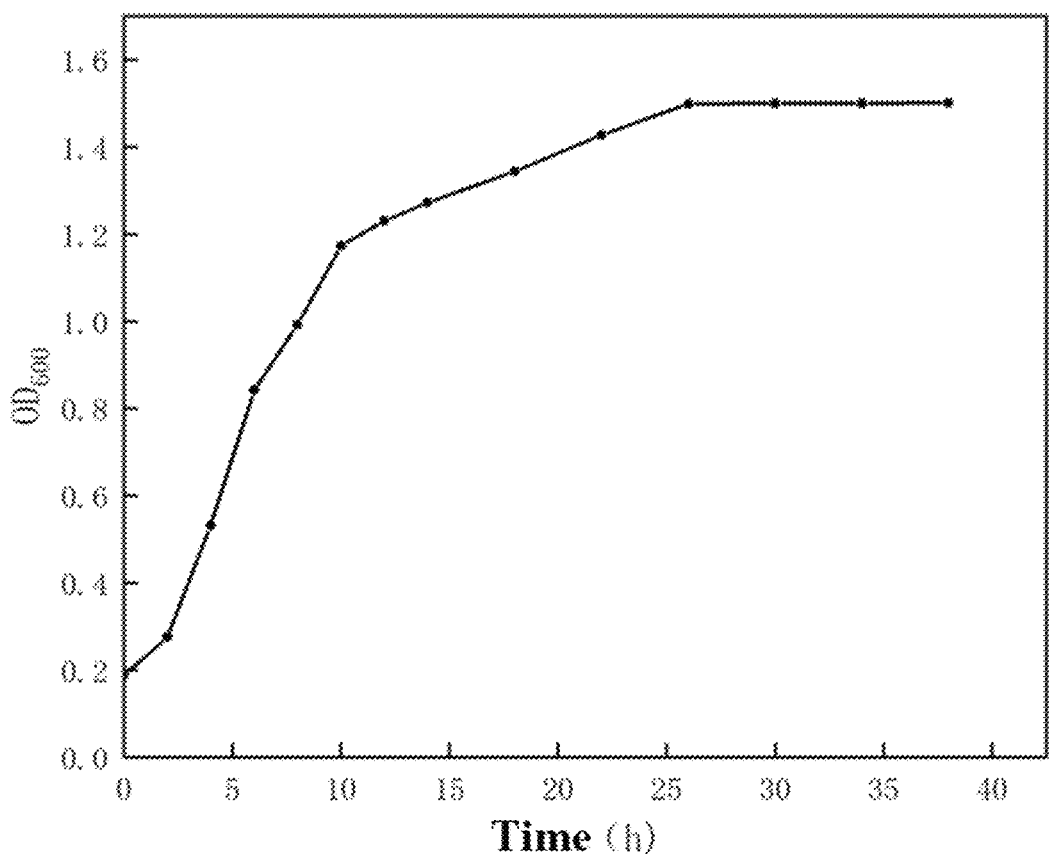
FIG. 3 is a growth curve of the bacterial strain obtained in Example 1.

The colony of the bacterial strain obtained in Example 1 on ocean 2216E solid culture medium was milky white, round in shape, smooth in surface and neat in edge, as shown in FIG. 2, which shows the morphology of the bacterial strain obtained in Example 1 on 2216E solid culture medium. Then the strain was inoculated into a 2216E liquid culture medium, and aerobically cultured at 28° C. and 120 rpm to determining its growth curve. The results are shown in FIG. 3 and Table 1. FIG. 3 is the growth curve of the bacterial strain obtained in Example 1, and Table 1 shows the data of the growth curve of the bacterial strain shown in FIG. 3. The 2216E liquid culture medium had a formula (/L) of: 5.0 g of peptone, 1.0 g of yeast powder, 0.1 g of ferric citrate, 19.45 g of sodium chloride, 5.98 g of magnesium chloride, 3.24 g of sodium sulfate, 1.8 g of calcium chloride, 0.55 g of potassium chloride, 0.16 g of sodium carbonate, 0.08 g of potassium bromide, 0.034 g of strontium chloride, 0.022 g of boric acid, 0.004 g of sodium silicate, 0.0024 g After a comprehensive comparison of the above features, the bacterial strain obtained in Example 1 was preliminarily identified as *Roseibium aggregatum* MY02 strain.

Example 3

In this example, the use of the *Roseibium aggregatum* MY02 of the present disclosure in degrading commercial polyethylene plastics is provided. The degradation and characterization were carried out by the following steps respectively (the culture medium used had the same formula as above and will not be repeated here):

1. Preparation of Seed Culture Solution

There were two methods. (1) A slant bacterial lawn of the *Roseibium aggregatum* MY02 of the present disclosure was inoculated into an inorganic salt liquid culture medium for a week of culture at 28° C. and 120 rpm to obtain a bacterial suspension, where the culture medium was adjusted to pH 7.0 with 1 mol/L NaOH, free of PE powder, and added with pre-sterilized polyethylene plastic film with a length and width of 1 cm at an amount of 2 g/L in advance (the treatment method was the same as that in Example 1). (2) A slant bacterial lawn of the *Roseibium aggregatum* MY02 of the present disclosure was inoculated into a 2216E liquid culture medium for 24 h of culture at 28° C. and 120 rpm to obtain a bacterial suspension, where the culture medium was added with sterile polyethylene plastic film with a length and width of 1 cm at an amount of 2 g/L in advance (the treatment method was the same as that in Example 1). The bacterial suspensions obtained in the two methods can be used as seed culture solutions. In this example, the growth curve of Example 2 was determined using the bacterial suspension obtained by the second method, and the degradation of polyethylene plastics, the measurement of the surface morphology by scanning electron microscope and the determination of functional groups in Example 3 were carried out by using the bacterial suspension obtained by the first method.

2. Expansion of Culture for Degrading Polyethylene Plastics

The seed culture solution was inoculated at an amount of 10% into an inorganic salt liquid culture medium added with polyethylene plastic film with a length and width of 1 cm at an amount of 2 g/L in advance to serve as a treatment group. An inorganic salt liquid culture medium added with polyethylene plastic film at an amount of 2 g/L in advance that was not inoculated with bacteria was used as a control group. The polyethylene films of the treatment group and the control group were both sterilized according to the method described in Example 1 in advance, and then weighed to a constant weight to obtain an initial weight of the polyethylene films. The treatment group and the control group were set up in three replicates. After 4 weeks of culture at 28° C. and 120 rpm, the loss of weight, changes in surface morphology, and changes in functional groups of the polyethylene plastic films were determined.

3. Quantitative and Qualitative Characterization of Degradation Effect on the Polyethylene Film 1) Method for determining degradation rate of the polyethylene film: The polyethylene films in the treatment group and control group were washed with 5% SDS under shaking for 5 h, ultrasonically washed for 30 min, soaked in 75% alcohol for 2 h, rinsed with sterile water for 3 times, then dried in an oven at 40° C. for 24 h, and weighed to a constant weight to obtain a weight of the polyethylene film after degradation by bacteria. The degradation rate was calculated according to the following formula: degradation rate=(initial weight of polyethylene film−weight of polyethylene film after degradation by bacteria)/(volume of culture solution× duration of degradation).

After 4 weeks of treatment with the *Roseibium aggregatum* MY02, the plastic film was degraded at a rate of 1.3±0.12 g/(d·m$^3$), whereas the control group showed no change in mass, indicating that the *Roseibium aggregatum* MY02 can effectively degrade polyethylene plastics.

Figure 4:
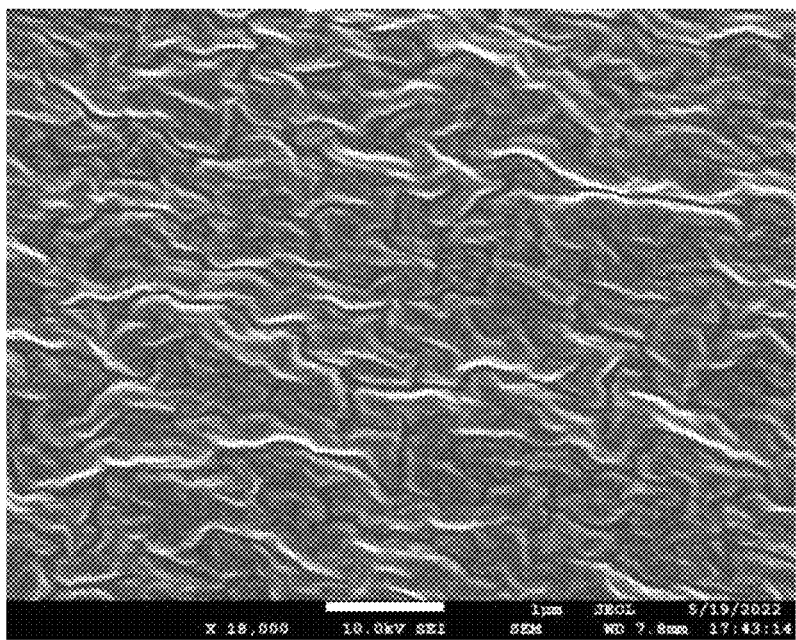
FIG. 4 shows the surface morphology of the polyethylene plastic film in the control group.
Figure 5:
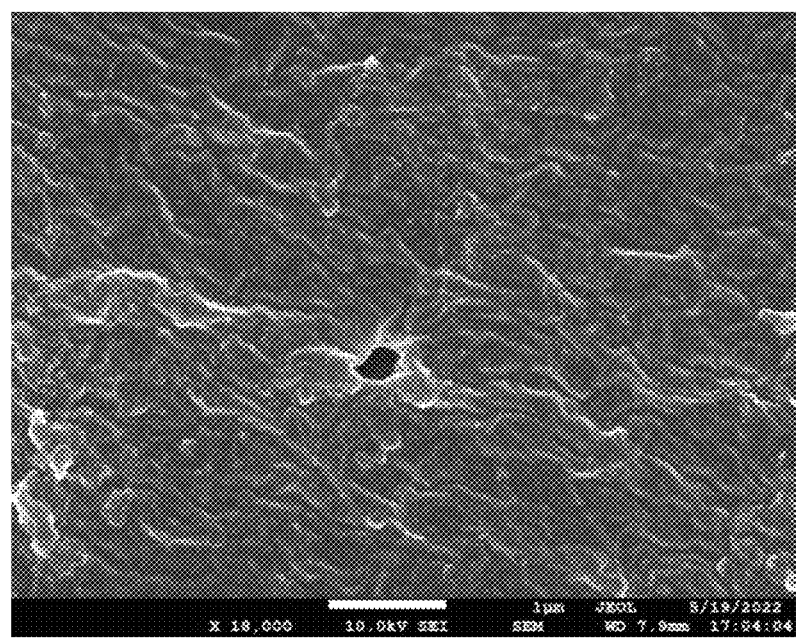
FIG. 5 shows the surface morphology of the polyethylene plastic film in the treatment group.

2) Observation of surface morphology of the polyethylene films: The polyethylene plastic films of the treatment group and the control group were respectively washed and dried according to the same method as in 1) above, and then sputtered with gold for 120 s to prepare samples for electron microscope observation. The surface morphology was observed by a field emission scanning electron microscope under conditions of a beam current of 40 mA and an accelerating voltage of 5 kV, as shown in FIGS. 4-5. FIG. 4 shows the surface morphology of the polyethylene plastic film in the control group, and FIG. 5 shows the surface morphology of the polyethylene plastic film in the treatment group. It can be seen from FIGS. 4-5 that the surface of the polyethylene plastic film in the treatment group became rough and exhibited obvious erosion holes, whereas the surface of the polyethylene plastic film in the control group without bacterial treatment showed no signs of erosion.

Figure 6:
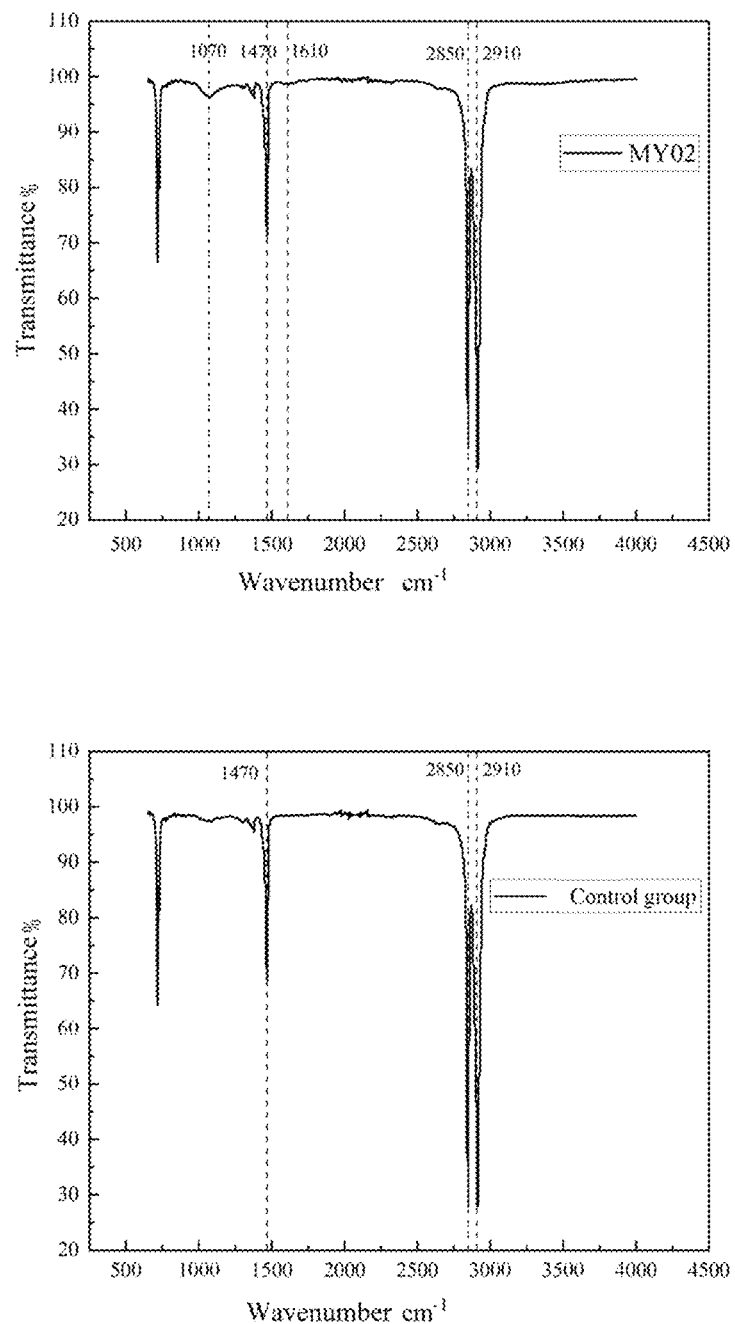
FIG. 6 is an infrared spectrogram of the polyethylene plastic films in the treatment and control groups.

Determination of functional groups of the polyethylene films: The polyethylene plastic films of the treatment group and control group were respectively washed and dried according to the same method as in 1) above. Determination was performed with a Fourier transform infrared spectrometer in ATR mode at a wavenumber range from 4000 cm$^{-1}$ to 400 cm$^{-1}$, 32 scans, and a resolution ratio of 4 cm$^{-1}$, and the result is shown in FIG. 6, which is an infrared spectrogram of the polyethylene plastic films of the treatment group and control group. Compared with the control group, in the treatment group, a carboxyl bond (COO—) was introduced at 1610 cm$^{-1}$, an unstable polar functional group carbon-oxygen bond (C—O extension) was introduced at 1070 cm$^{-1}$, the absorption peaks of bending vibration and symmetric stretching vibration of carbon-hydrogen bond (CH$_2$—) at 1470 cm$^{-1}$ and 2850 cm$^{-1}$ were weakened, CH$_2$— structure in the main chain was reduced, and the main chain is possible to be cut off, indicating that the *Roseibium aggregatum* MY02 in the treatment group had chemical degradation effect on polyethylene film.

The above are only preferred embodiments of the present disclosure, but the scope of the present disclosure is not limited thereto. Within the technical scope disclosed in the present disclosure, any person skilled familiar with the technical field can make equivalent replacements or changes according to the technical solution and inventive concept of the present disclosure, which shall all fall within the scope of the present disclosure.

The invention claimed is:

1. A method for degrading plastics, comprising:
   contacting polyethylene plastic with a strain *Roseibium aggregatum* MY02, which has an accession number of CGMCC No. 25240,
   wherein the contacting is conducted by inoculating the strain *Roseibium aggregatum* MY02 in a culture medium containing polyethylene plastic and culturing, wherein a mass of the polyethylene plastic contained in each liter of the culture medium is 1 g to 3 g, and the strain *Roseibium aggregatum* MY02 is inoculated at an amount of 5%-20% of the culture medium.

2. The method according to claim 1, wherein the culturing is performed at a pH value of 6-8.

3. The method according to claim 1, wherein the culturing is performed at 10° C.-40° C. and 100 rpm-150 rpm.

4. The method according to claim 1, wherein, in parts by mass, the culture medium comprises:
   0.5-1 part of K$_2$HPO$_4$, 0.5-1 part of KH$_2$PO$_4$, 0.8-1.2 parts of NH$_4$NO$_3$, 0.08-0.12 parts of CaCl$_2$, 0.01-0.04 parts of FeSO$_4$ and 500-1500 parts of seawater;
   or,
   0.5-1 part of K$_2$HPO$_4$, 0.5-1 part of KH$_2$PO$_4$, 0.8-1.2 parts of NH$_4$NO$_3$, 0.08-0.12 parts of CaCl$_2$, 0.01-0.04 parts of FeSO$_4$, 10-20 parts of agar and 500-1500 parts of seawater.

5. The method according to claim 1, wherein the strain *Roseibium aggregatum* MY02 is subjected to enrichment culture in an enrichment culture medium before inoculation; and
   in parts by mass, the enrichment culture medium comprises 0.5-1 part of K$_2$HPO$_4$, 0.5-1 part of KH$_2$PO$_4$, 0.8-1.2 parts of NH$_4$NO$_3$, 0.08-0.12 parts of CaCl$_2$, 0.01-0.04 parts of FeSO$_4$, 0.08-0.12 parts of yeast extract powder and 500-1500 parts of seawater.

* * * * *